United States Patent
Guenst et al.

(10) Patent No.: US 7,438,680 B2
(45) Date of Patent: *Oct. 21, 2008

(54) METHOD AND DEVICE FOR ORGAN POSITIONING

(75) Inventors: Gary W. Guenst, Collegeville, PA (US); Christopher Olig, Eden Prairie, MN (US); Paul A. Pignato, Stacy, MN (US); Karen Montpetit, Mendota Heights, MN (US); Thomas Daigle, Corcoran, MN (US); Douglas H. Gubbin, Brooklyn Park, MN (US); Scott E. Jahns, Hudson, WI (US); Katherine Jolly, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1081 days.

This patent is subject to a terminal disclaimer.

(21) Appl. No.: 10/654,040

(22) Filed: Sep. 3, 2003

(65) Prior Publication Data

US 2004/0055125 A1 Mar. 25, 2004

Related U.S. Application Data

(63) Continuation of application No. 09/879,293, filed on Jun. 12, 2001, now Pat. No. 6,676,597.

(60) Provisional application No. 60/286,952, filed on Apr. 26, 2001, provisional application No. 60/282,029, filed on Apr. 6, 2001, provisional application No. 60/263,739, filed on Jan. 24, 2001, provisional application No. 60/261,343, filed on Jan. 13, 2001.

(51) Int. Cl.
*A61F 2/00* (2006.01)

(52) U.S. Cl. .................................................. 600/37

(58) Field of Classification Search .................. 600/37, 600/231–234, 201, 210, 227–229, 235; 128/897, 128/898; 606/1, 166, 191, 158.1, 108
See application file for complete search history.

(56) References Cited

U.S. PATENT DOCUMENTS 452,131 A 5/1891 Haughawout (Continued)

FOREIGN PATENT DOCUMENTS

EP 0 167 345 A1 1/1986

(Continued)

OTHER PUBLICATIONS

Mammary Artery-Coronary Artery Anastomosis as Method of Treatment for Angina Pectoris, V.I Kolessov, MD/Thoracic and Cardiovascular Surgery, vol. 54, No. 4, Oct. 1967 pp. 535-544.

(Continued)

*Primary Examiner*—Samuel G Gilbert
(74) *Attorney, Agent, or Firm*—Mike Jaro; Jeffrey J. Hohenshell

(57) ABSTRACT

This invention provides an organ positioning device and method that employs suction to hold organ tissue to the device. The device allows the organ, for example, heart to be positioned in a desired orientation but otherwise allowing movement of the heart as the heart beats. The device is designed to be relatively atraumatic to heart tissue. Generally, the device comprises a resiliently flexible suction head having a plurality of legs that flex to conform to the surface of the heart. The suction head has vacuum passageways in fluid communication with the legs to apply suction between the legs and the surface of the heart.

41 Claims, 14 Drawing Sheets

U.S. PATENT DOCUMENTS

| | | |
|---|---|---|
| 2,590,527 A | 3/1952 | Fluck |
| 3,577,982 A | 5/1971 | La Par |
| 3,720,433 A | 3/1973 | Rosfelder |
| 3,783,873 A | 1/1974 | Jacobs |
| 3,786,815 A | 1/1974 | Ericson |
| 3,858,926 A | 1/1975 | Ottenhues |
| 3,916,909 A | 11/1975 | Kletschka et al. |
| 3,951,138 A | 4/1976 | Akopov |
| 3,983,863 A | 10/1976 | Janke et al. |
| 3,999,795 A | 12/1976 | Barker |
| 4,047,532 A | 9/1977 | Phillips et al. |
| 4,049,000 A | 9/1977 | Williams |
| 4,049,002 A | 9/1977 | Kletschka et al. |
| 4,096,864 A | 6/1978 | Kletschka et al. |
| 4,306,561 A | 12/1981 | De Medinaceli |
| 4,314,568 A | 2/1982 | Loving |
| 4,350,160 A | 9/1982 | Kolesov |
| 4,366,819 A | 1/1983 | Kaster |
| 4,368,736 A | 1/1983 | Kaster |
| 4,428,368 A | 1/1984 | Torii |
| 4,447,227 A | 5/1984 | Kotsanis |
| 4,463,980 A | 8/1984 | Orii |
| 4,627,421 A | 12/1986 | Symbas et al. |
| 4,637,377 A | 1/1987 | Loop |
| 4,646,747 A | 3/1987 | Lundbáck |
| 4,688,570 A | 8/1987 | Kramer et al. |
| 4,711,247 A | 12/1987 | Fishman |
| 4,718,418 A | 1/1988 | L'Esperance, Jr. |
| 4,726,356 A | 2/1988 | Santilli et al. |
| 4,736,749 A | 4/1988 | Lundback |
| 4,767,142 A | 8/1988 | Takahashi et al. |
| 4,808,163 A | 2/1989 | Laub |
| 4,852,552 A | 8/1989 | Chaux |
| 4,854,318 A | 8/1989 | Solem et al. |
| 4,865,019 A | 9/1989 | Phillips |
| 4,892,343 A | 1/1990 | Hall |
| 4,904,012 A | 2/1990 | Nishiguchi et al. |
| 4,925,443 A | 5/1990 | Heilman et al. |
| 4,955,896 A | 9/1990 | Freeman |
| 4,962,758 A | 10/1990 | Lasner et al. |
| 4,973,300 A | 11/1990 | Wright |
| 4,989,587 A | 2/1991 | Farley |
| 4,991,578 A | 2/1991 | Cohen |
| 5,009,660 A | 4/1991 | Clapham |
| 5,011,469 A | 4/1991 | Buckberg et al. |
| 5,053,041 A | 10/1991 | Ansari et al. |
| 5,098,369 A | 3/1992 | Heilman et al. |
| 5,108,412 A | 4/1992 | Krumeich et al. |
| 5,119,804 A | 6/1992 | Anstadt |
| 5,131,905 A | 7/1992 | Grooters |
| 5,133,737 A | 7/1992 | Grismer |
| 5,167,223 A | 12/1992 | Koros et al. |
| 5,171,254 A | 12/1992 | Sher |
| 5,207,467 A | 5/1993 | Smith |
| 5,287,861 A | 2/1994 | Wilk |
| 5,290,082 A | 3/1994 | Palmer et al. |
| 5,300,087 A | 4/1994 | Knoepfler |
| 5,324,087 A | 6/1994 | Shimose et al. |
| 5,336,252 A | 8/1994 | Cohen |
| 5,365,921 A | 11/1994 | Bookwalter et al. |
| 5,372,124 A | 12/1994 | Takayama et al. |
| 5,374,277 A | 12/1994 | Hassler |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,472,438 A | 12/1995 | Schmit et al. |
| 5,503,617 A | 4/1996 | Jako |
| 5,509,890 A | 4/1996 | Kazama |
| 5,545,123 A | 8/1996 | Ortiz et al. |
| 5,556,147 A | 9/1996 | Somekh et al. |
| 5,607,421 A | 3/1997 | Jeevanandam et al. |
| 5,613,937 A | 3/1997 | Garrison et al. |
| 5,667,624 A | 9/1997 | Akimoto et al. |
| 5,702,420 A | 12/1997 | Sterling et al. |
| 5,727,569 A | 3/1998 | Benetti et al. |
| 5,730,757 A | 3/1998 | Benetti et al. |
| 5,749,892 A | 5/1998 | Vierra et al. |
| 5,772,583 A | 6/1998 | Wright et al. |
| 5,782,746 A | 7/1998 | Wright |
| 5,799,661 A | 9/1998 | Boyd et al. |
| 5,807,243 A | 9/1998 | Vierra et al. |
| 5,827,216 A | 10/1998 | Igo et al. |
| 5,836,311 A | 11/1998 | Borst et al. |
| 5,865,730 A | 2/1999 | Fox et al. |
| 5,875,782 A | 3/1999 | Ferrari et al. |
| 5,876,332 A | 3/1999 | Looney |
| 5,885,271 A * | 3/1999 | Hamilton et al. ............... 606/1 |
| 5,888,247 A | 3/1999 | Benetti |
| 5,891,017 A | 4/1999 | Swindle et al. |
| 5,894,843 A | 4/1999 | Benetti et al. |
| 5,906,607 A | 5/1999 | Taylor et al. |
| 5,927,284 A | 7/1999 | Borst et al. |
| 5,947,896 A | 9/1999 | Sherts et al. |
| 5,957,835 A | 9/1999 | Anderson et al. |
| 5,967,972 A | 10/1999 | Santilli et al. |
| 5,976,080 A | 11/1999 | Farascioni |
| 5,976,171 A | 11/1999 | Taylor |
| 5,984,864 A | 11/1999 | Fox et al. |
| 6,007,486 A | 12/1999 | Hunt et al. |
| 6,015,378 A | 1/2000 | Borst et al. |
| 6,017,304 A | 1/2000 | Vierra et al. |
| 6,019,722 A * | 2/2000 | Spence et al. ............... 600/210 |
| 6,030,340 A | 2/2000 | Maffei et al. |
| 6,032,672 A | 3/2000 | Taylor |
| 6,033,362 A | 3/2000 | Cohn |
| 6,036,641 A | 3/2000 | Taylor et al. |
| 6,050,266 A | 4/2000 | Benetti et al. |
| 6,063,021 A | 5/2000 | Hossain et al. |
| 6,071,235 A | 6/2000 | Furnish et al. |
| 6,071,295 A | 6/2000 | Takahashi |
| 6,102,854 A | 8/2000 | Cartier et al. |
| 6,110,187 A | 8/2000 | Donlon |
| 6,113,534 A | 9/2000 | Koros et al. |
| 6,139,492 A | 10/2000 | Vierra et al. |
| 6,152,874 A | 11/2000 | Looney et al. |
| 6,210,323 B1 | 4/2001 | Gilhuly et al. |
| 6,213,941 B1 | 4/2001 | Benetti et al. |
| 6,238,334 B1 | 5/2001 | Easterbrook, III et al. |
| 6,251,065 B1 | 6/2001 | Kochamba et al. |
| 6,258,023 B1 | 7/2001 | Rogers et al. |
| 6,371,910 B1 | 4/2002 | Zwart et al. |
| 6,394,951 B1 | 5/2002 | Taylor et al. |
| 6,488,618 B1 | 12/2002 | Paolitto et al. |
| 6,503,245 B2 | 1/2003 | Palmer et al. |
| 6,506,149 B2 | 1/2003 | Peng et al. |
| 6,511,416 B1 | 1/2003 | Green, II et al. |
| 6,551,242 B1 | 4/2003 | Furnish et al. |
| 6,558,314 B1 | 5/2003 | Adelman et al. |
| 6,585,643 B2 | 7/2003 | Clem et al. |
| 6,589,166 B2 | 7/2003 | Knight et al. |
| 6,602,183 B1 | 8/2003 | Levi et al. |
| 6,602,189 B1 | 8/2003 | Bennetti et al. |
| 6,607,479 B1 | 8/2003 | Kochamba et al. |
| 6,676,597 B2 * | 1/2004 | Guenst et al. ................. 600/37 |
| 2001/0041827 A1 | 11/2001 | Spence et al. |
| 2002/0099268 A1 | 7/2002 | Paul et al. |
| 2002/0137989 A1 | 9/2002 | Clem et al. |
| 2002/0165434 A1 | 11/2002 | Williamson, IV et al. |
| 2003/0083554 A1 | 5/2003 | Paolitto et al. |
| 2003/0088150 A1 | 5/2003 | Green, II et al. |

| | | | |
|---|---|---|---|
| 2003/0125604 | A1 | 7/2003 | Kochamba et al. |

FOREIGN PATENT DOCUMENTS

| | | |
|---|---|---|
| EP | 0 293 760 A3 | 5/1988 |
| EP | 0 630 629 A1 | 12/1994 |
| EP | 0 668 058 A1 | 8/1995 |
| EP | 0 808 606 A1 | 11/1997 |
| EP | 0 908 139 A1 | 4/1999 |
| EP | 0 919 193 A1 | 6/1999 |
| EP | 0 920 835 A1 | 6/1999 |
| EP | 0993806 A2 | 4/2000 |
| EP | 0993806 A3 | 6/2000 |
| GB | 2 140 695 A | 12/1984 |
| GB | 2 214 428 A | 9/1989 |
| GB | 2 233 561 | 1/1991 |
| GB | 2 214 428 B | 6/1991 |
| GB | 2267827 | 12/1993 |
| WO | WO 87/04081 | 7/1987 |
| WO | WO 88/00481 | 1/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/40751 | 11/1997 |
| WO | WO 98/10705 | 3/1998 |
| WO | WO 98/17182 | 4/1998 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/15119 | 3/2000 |
| WO | WO 03/001969 | 1/2003 |
| WO | WO 03/001998 | 1/2003 |

OTHER PUBLICATIONS

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974-978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108-109.

A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2 Aug. 1979, pp. 269-273.

Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304-310.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52-57.

Direct Myocardial Revascularization Without Cardiopulmonary Bypass, E. Buffolo; JCS Andrade, J Succi; Lev Leao; and C Gallucci. Thoac. Cardiovasc. Surgeon, 33 (1985) pp. 26-29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May-Jun. 1985, pp. 217-222.

Heart-Mechanical Assist Device Interaction, JY Kresh; PLM Kerkhof; SM Goldman; and SK Brockman, Trans. Am. Soc. Artif. Intern. Organs, vol. XXXII, 1986, pp. 437-443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710-712.

Long-Term Follow-up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116-124.

Extended Clinical Support with an Implantable Left Ventricular Assist Device, MG McGee; SM Parnis; T Nakatani; T Myers, K Dasse; WD Hare; JM Duncan; VL Poirier; and OH Frazier, Trans Am. Soc. Artif. Intern. Organs, vol. XXXV, 1989, pp. 614-616.

Current Status of Cardiac Surgery: A 40-Year Review, WE Richenbacher, MD; JL Myers, MD, FACC; JA Walhausen, MD, FACC, Journal of American College of Cardiology, vol. 14, No. 3, Sep. 1989, pp. 535-544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69-72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312-316.

Coronary Artery Bypass Without Cardiopulmonary Bypass, Pfister et al, The Annals of Thoracic Surgery, vol. 54 # 6 Dec. 1992 pp. 1085-1092.

Coronary Artery Operation Supported by the Hemopump: An Experimental Study on Pig, U Lonn, MD; B Peterzen, MD; H Granfeldt, MD; and H Casimir-Ahn, MD, Ph.D. The Annals of Thoracic Surgery, vol. 58, No. 1, Jul. 1994, pp. 516-523.

Regional Cardiac Wall Immobilization for Open Chest and Closed Chest Coronary Artery Bypass Grafting on the Beating Heart: The 'Octopus' Method, Circulation, vol. 92. No. 8 Supplement 1, I-177 (Oct. 15, 1995).

A. Minimally Invasive Surgical Method for Coronary Revascularization—Preliminary Experience in Five Patients, MC Robinson, DR Gross, and W Zeman, Circulation, (Oct 15, 1995) vol. 92, No. 8, I-176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356-1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486-489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570-575.

Transcatheter Radiofrequency Ablation of Atrial Tissue Using a Suction Catheter, Th Lavergne et al. (PACE, vol. 12, Jan. 1989, Part II, pp. 177-186.

Placement of Coronary Artery Bypass Graft without Pump Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Gründerman; DW Meijer; JJG Bannenberg; R rukkie; and PJ Klopper, Surgical Endoscopy (1993) 7: 511-513.

The LAST Operation: Techniques and Results Before and After the Stabilization Era, Antonio M. Calafiore, MD; Giuseppe Vitolla, MD; Valerio Massei, MD; Giovanni Teodori, MD; Gabriele Di Giammarco, MD; Teresa Iovino, MD and Angela Iaco, MD; Ann Thorac Surg 1998; 66:998-1001.

Hybrid-Type Stabilizer for Off-Pump Direct Coronary Artery Bypass Grafting, by: Toshio Konishi, M.D.; Kazuhiko Higuchi, M.D.; Mutumu Fukata, M.D.; Shinji Akisima, M.D.; and Shiji Fukuda, M.D.; Ann Thorac Surgery 1998; 66:961-2.

A.J. Delrossi, M.D., and G.M. Lemore, M.D., A New Retractor to Aid in Coronary Artery Surgery, The Annals of Thoracic and Cardiovascular Surgery, vol. 36 Jul. 1983, pp. 101-102.

Stephen Westaby, Frcs and Federico J. Benetti, M.D.; Less Invasive Coronary Surgery: Consensus from the Oxford Meeting, Annals of Thoracic Surgery 1996, 62: 924-31.

Kolessov V.I. The Surgery of Coronary Arteries of the Heart, Leningrad, Meditsina, 1977, pp. 360. (Russian Article).

Kolessov V.I. The Surgery of Coronary Arteries of the Heart, Leningrad, Meditsina, 1977, pp. 360. (English Translation).

New Helper Instrument in Cardiac Surgery—D. Roux, M.D.; G. Fournial, M.D.; Y. Glock, M.D.; P. Dalous, M.D.; and P. Puel, M.D., Annal Thorac Surg. 1989;48:595-6.

* cited by examiner

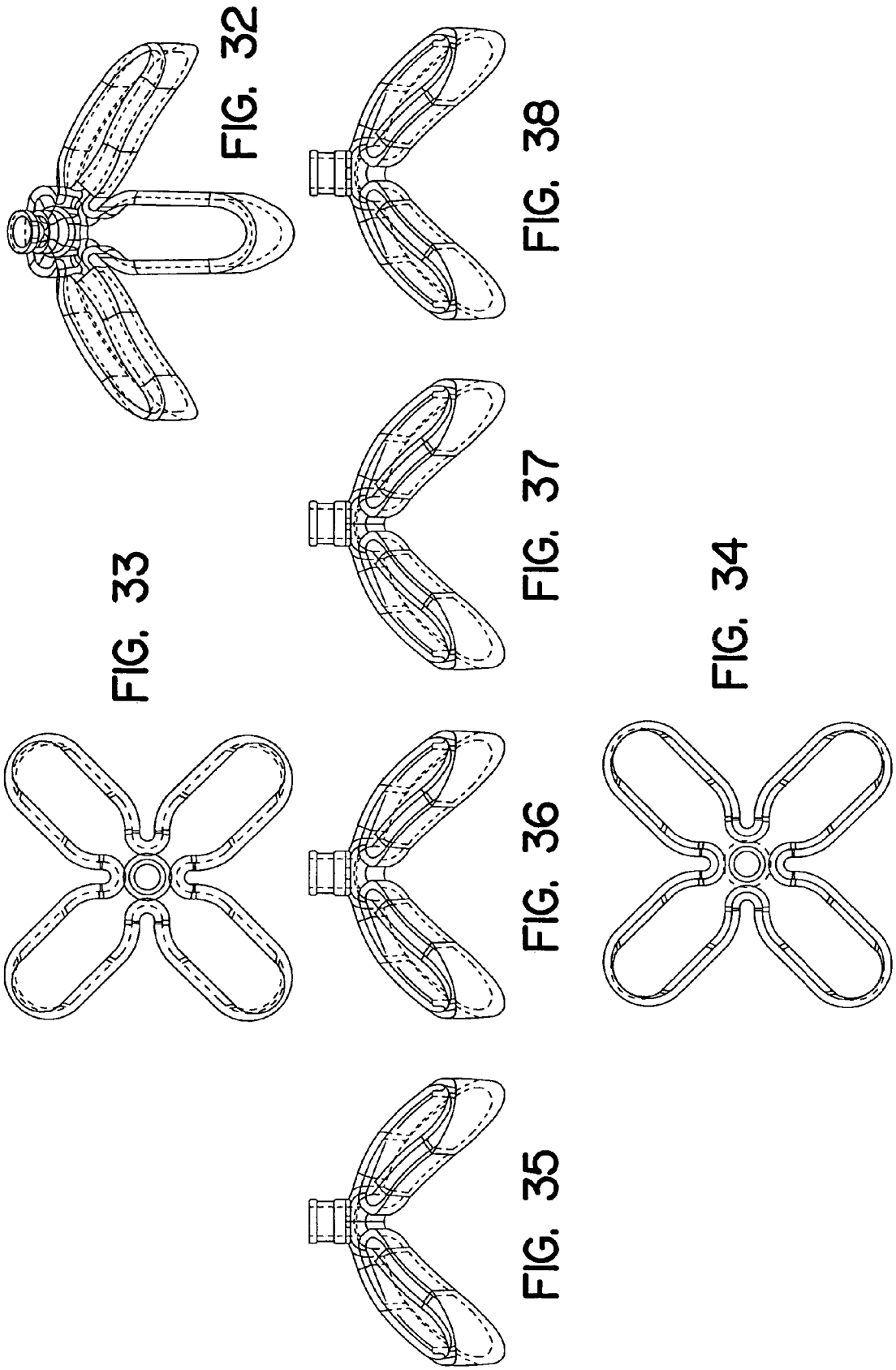

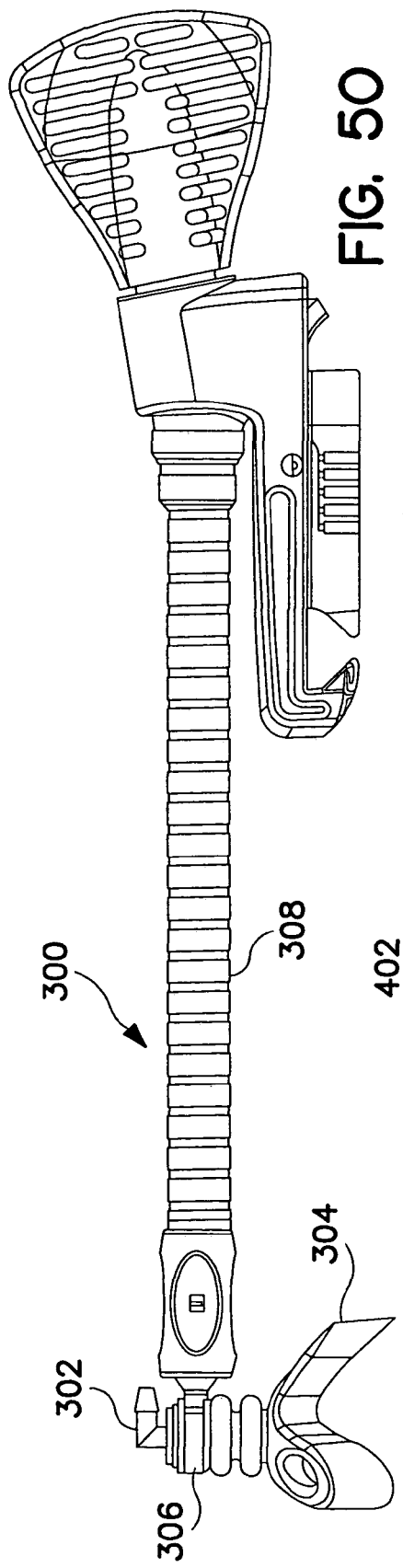
FIG. 50
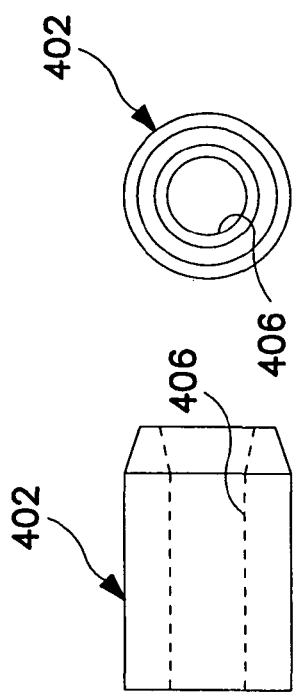
FIG. 52
FIG. 53
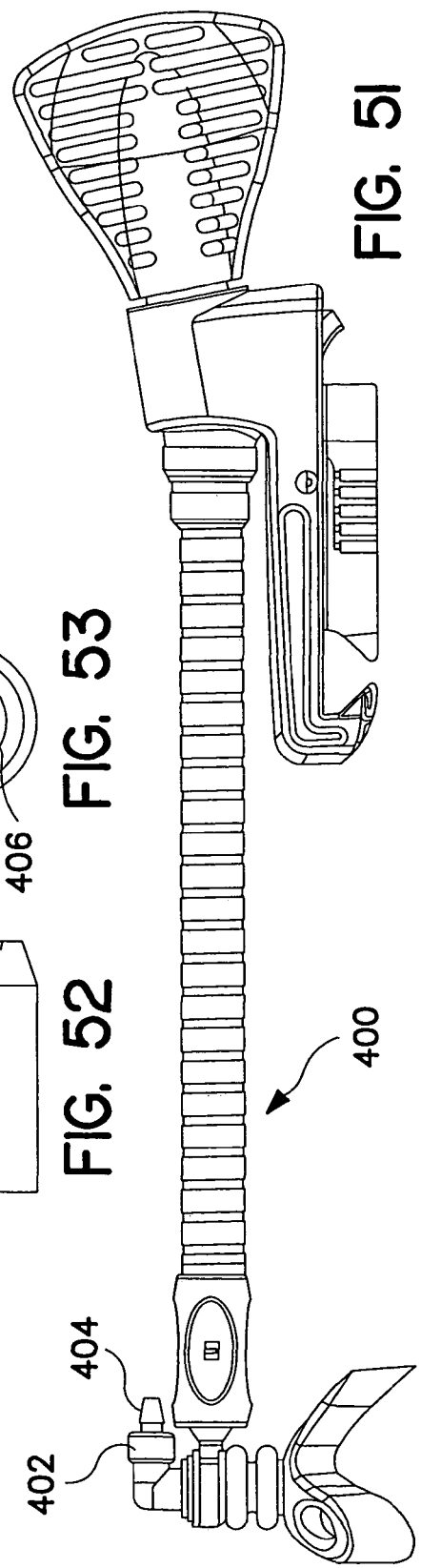
FIG. 51

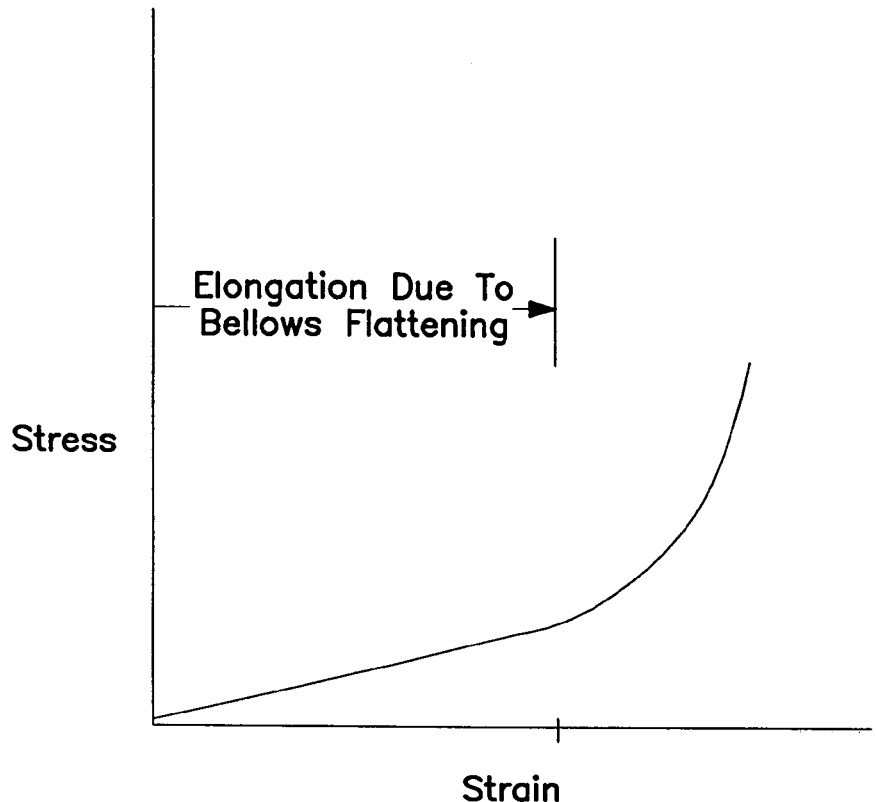
FIG. 54
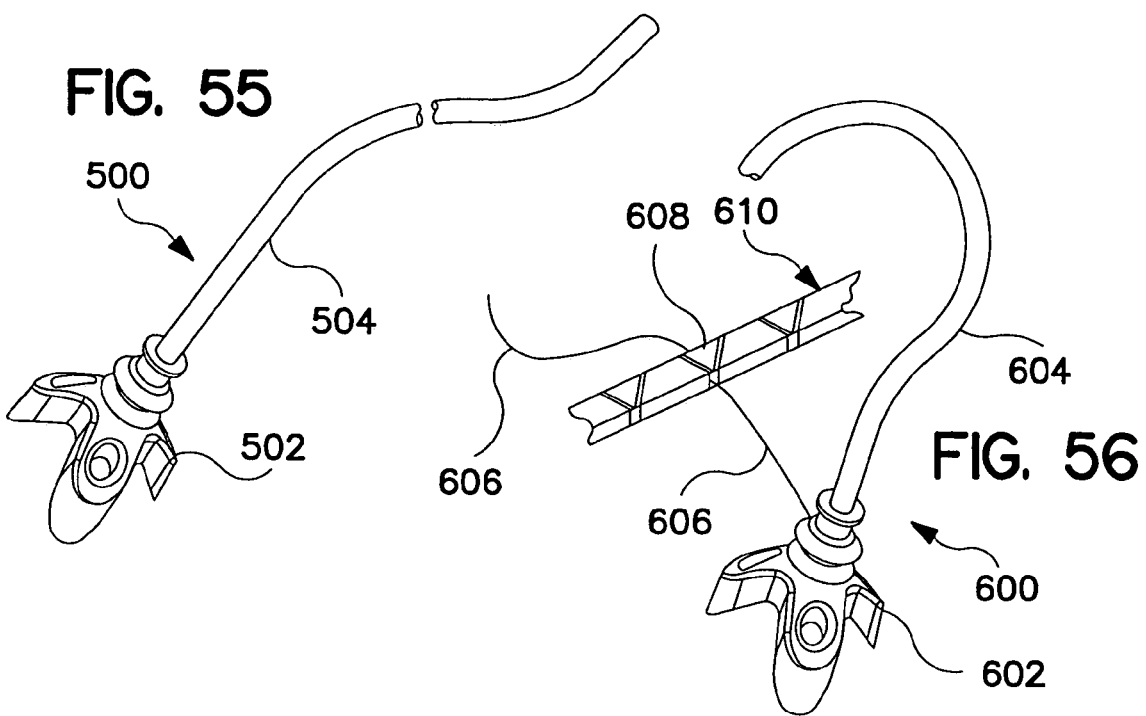
FIG. 55
FIG. 56

METHOD AND DEVICE FOR ORGAN POSITIONING

CROSS-REFERENCE TO RELATED APPLICATIONS

This application is a continuation of application Ser. No. 09/879,293 filed Jun. 12, 2001, now U.S. Pat. No. 6,676,597 issued Jan. 1, 2004, and also claims priority to co-owned U.S. Provisional Patent Applications Ser. No. 60/261,343 filed Jan. 13, 2001, Ser. No. 60/263,739 filed Jan. 24, 2001, Ser. No. 60/282,029 filed Apr. 6, 2001, and Ser. No. 60/286,952 filed Apr. 26, 2001, the disclosures of which are incorporated herein by reference.

FIELD OF THE INVENTION

This invention relates generally to a system and method for positioning an organ, and more particularly to a system capable of positioning, manipulating, stabilizing and/or holding a heart during cardiac surgery. This invention also relates to a positioning system and method that includes monitoring one or more chemical, physical or physiological characteristics of a bodily tissue or fluid during a medical procedure.

BACKGROUND OF THE INVENTION

This invention relates generally to a device and method for positioning an organ, such as the heart, and more particularly to a suction device for grasping, orienting and/or positioning an organ, such as the heart during cardiac surgery.

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally consists of the following steps: First, direct access to the heart is achieved. This is usually done by opening the chest by median sternotomy and spreading the left and right rib cage apart; and opening the pericardial sac to achieve direct access to the heart.

Next, a blood vessel or vessels for use in the graft procedure are mobilized from the patient. This usually entails mobilizing either a mammary artery or a saphenous vein, although other graft vessels may also be used.

Next, a heart-lung or cardiopulmonary bypass is performed. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

One area which may create difficulties for the patient and extra expense and time for the procedure involves the cardiopulmonary bypass. In a cardiopulmonary bypass all the patient's blood, which normally returns to the right atrium, is diverted to a system which supplies oxygen to the blood and removes carbon dioxide and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1-9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (February 1993) pgs. 486-489 also reported immobilizing the area of the bypass graft with stabilization sutures.

Suction stabilization systems, such as the Medtronic OCTOPUS® Tissue Stabilizer and Accessories (available from Medtronic, Inc., Minneapolis, Minn. USA), the current model being designated the "OCTOPUS 3™ stabilization system", use suction to grip and immobilize the surface of the heart. Additionally, the system allows the surgeon to manipulate the anastomosis site into better view by rotating and supporting the heart. See, also, e.g., U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806. The OCTOPUS™ stabilizer facilitates moving or repositioning the heart to achieve better access to areas which would otherwise be difficult to access, such as the posterior or backside of the heart.

SUMMARY OF THE INVENTION

This invention provides an organ positioning device and method that employs suction to hold organ tissue to the device. The device allows the organ, for example, heart to be positioned in a desired orientation but otherwise allowing movement of the heart as the heart beats. The device is designed to be relatively atraumatic to heart tissue.

Generally, a heart positioning device of the present invention comprises a resiliently-flexible suction pad or head having a plurality of legs that flex to conform to the surface of the heart. The suction pad has vacuum passageways in fluid communication with the legs to apply suction between the legs and the surface of the heart. A vacuum line is connected to the vacuum passageway. A support arm is connected to the suction pad to position the suction pad to thereby position or hold the heart.

The suction pad preferably is generally starfish-shaped in addition to being resiliently flexible so that the legs flex to conform and/or collapse partly or completely to the surface of the heart, and can be attached with suction to the heart at the apex of the heart or elsewhere along the heart. The starfish shape also allows the suction pad to be oriented relative to the anatomy of the heart, for example, to improve access to an artery.

A second aspect of the invention is the method of use of the device to position or orient the heart during cardiac surgery, such as but not limited to open-chest, beating-heart surgery.

In a third aspect of the invention, a heart positioning device generally comprises a suction head having a vacuum passageway for applying suction between the suction head and the surface of the heart, a vacuum line connected to the vacuum passageway, a support arm connected to the suction head to position the suction head to thereby position or hold the heart, and a bellows-type suspension element connecting the suction head and support arm. The bellows-type suspension element flexes to allow the suction head to move in response to beating of the heart.

A fourth aspect of the invention is a suction head for use in a heart positioning device. The suction head is formed of resiliently flexible material. The suction head has at least one vacuum passageway for applying suction to the surface of the heart, and a resiliently flexible peripheral flange. The suction head and/or flange is sufficiently resiliently flexible that the suction head draws down toward the surface of the heart more than the surface of the heart is pulled into the suction head.

A fifth aspect of the invention is a suction head having a porous material such as a porous membrane, screen, mesh, open cell foam, fabric or the like intermediate between the tissue and vacuum orifice to prevent the vacuum orifice and tissue from being drawn together and closing the orifice. This is particularly important for fatty tissues on the heart that may be pulled into the suction head and block the fluid communication between the vacuum passageway and the vacuum channels. During operation of the device, the porous material may engage tissue and may be provided with a textured surface to improve frictional contact with the tissue.

The device may be used, for example, in combination with a heart stabilizer, such as the stabilization system sold under the trade designation "OCTOPUS 3"™ by Medtronic, Inc., Fridley, Minn., USA. See, also, e.g., U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000.

BRIEF DESCRIPTION OF THE DRAWINGS

The invention will be further described with reference to the drawing wherein corresponding reference characters indicate corresponding parts throughout the several views of the drawing, and wherein:

FIG. 32 is a perspective view of a fourth alternative embodiment of the suction pad;

FIG. 33 is a top view of the suction pad of FIG. 32;

FIG. 34 is a bottom view of the suction pad of FIGS. 32 and 33;

FIGS. 35-38 are front, right, back and left side views of the suction pad of FIGS. 32-34;

FIGS. 50 and 51 is a side views of further embodiments of the heart positioner of the invention;

FIG. 52 is a side view of a filter element provided in the heart positioner of FIG. 51;

FIG. 53 is an end view of the filter of FIG. 52;

FIG. 54 is a stress strain graph generally illustrating spring rates of a bellows-type suspension element of a preferred suction head or pad;

FIGS. 55 and 56 are perspective views of additional preferred embodiments of the heart positioner of the invention;

DETAILED DESCRIPTION OF PREFERRED EXEMPLARY EMBODIMENTS

Figure 1:
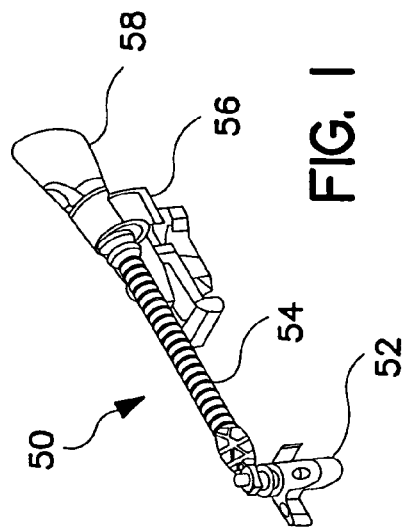
FIG. 1 is a perspective view of a preferred embodiment of the heart positioning device of the invention.
Figure 2:
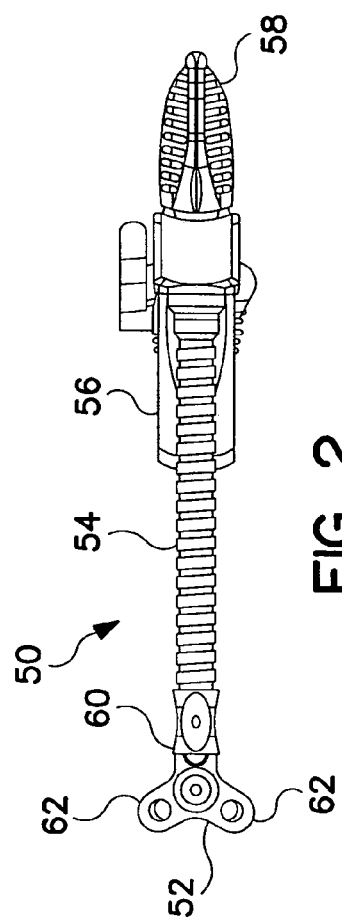
FIG. 2 is a top view of the device of FIG. 1.
Figure 3:
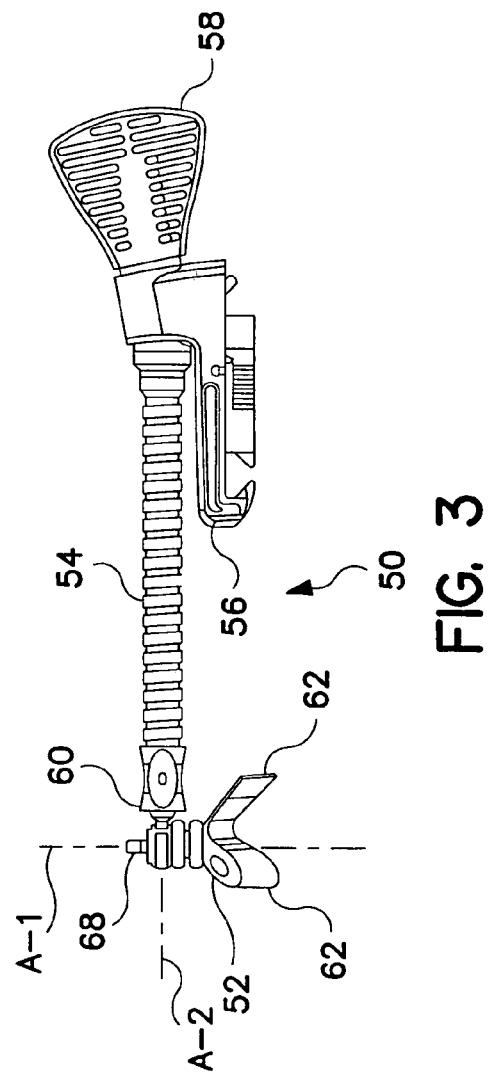
FIG. 3 is a side view of the device of FIGS. 1 and 2.
Figure 4:
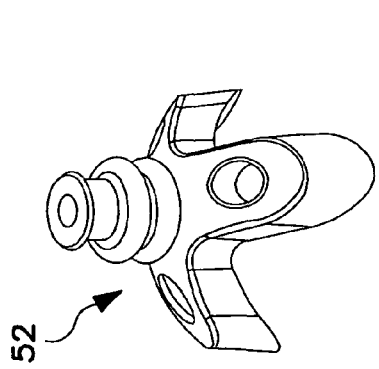
FIG. 4 is a perspective view of a preferred embodiment of the suction pad of the device of FIGS. 1-3.
Figure 5:
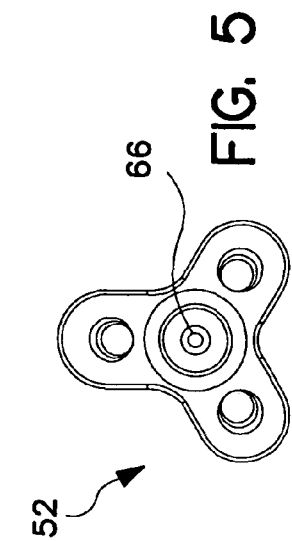
FIG. 5 is a top view of the suction pad of FIG. 4.
Figure 8:
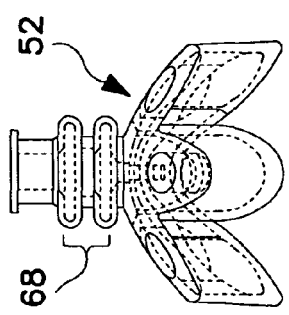
FIGS. 7-10 are front, right, back and left side views of the suction pad of FIGS. 4-6.
Figure 10:
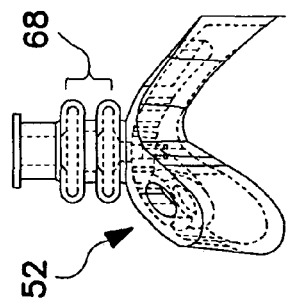
Figure 9:
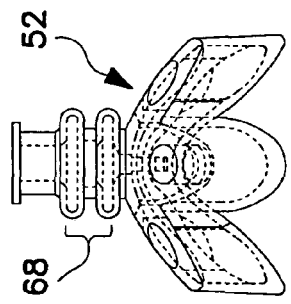
Figure 7:
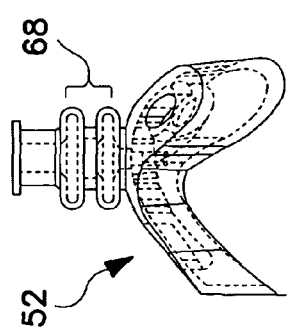
Figure 6:
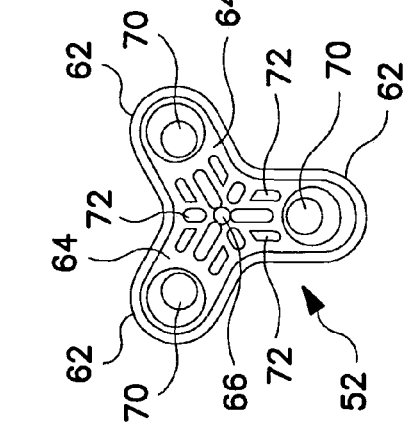
FIG. 6 is a bottom view of the suction pad of FIGS. 4 and 5.
Figure 11:
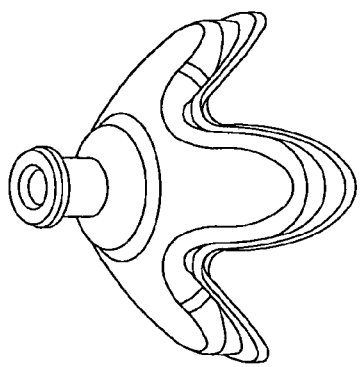
FIG. 11 is a perspective view of a first alternative embodiment of the suction pad.
Figure 12:
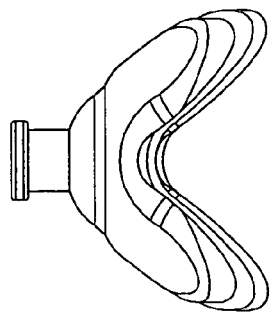
FIG. 12 is a top view of the suction pad of FIG. 11.
Figure 17:
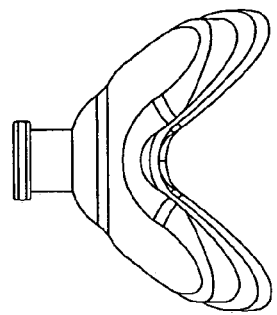
FIGS. 14-17 are front, right, back and left side views of the suction pad of FIGS. 11-13.
Figure 15:
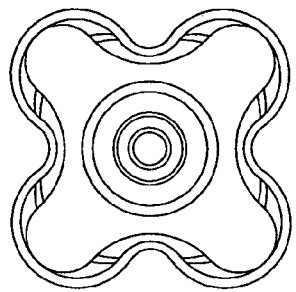
Figure 16:
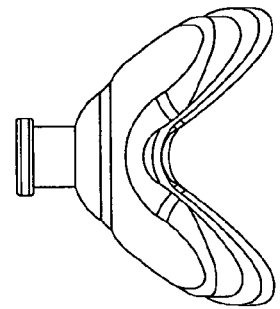
Figure 13:
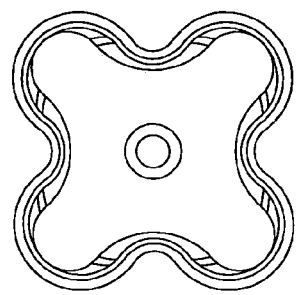
FIG. 13 is a bottom view of the suction pad of FIGS. 11 and 12.
Figure 14:
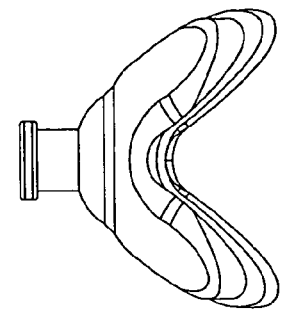
Figure 18:
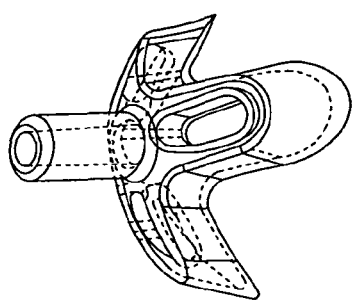
FIG. 18 is a perspective view of a second alternative embodiment of the suction pad.
Figure 24:
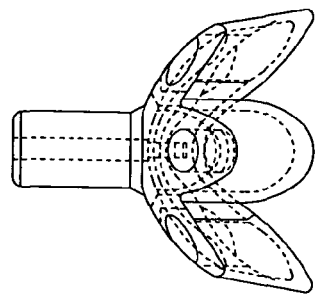
FIGS. 21-24 are front, right, back and left side views of the suction pad of FIGS. 18-20.
Figure 23:
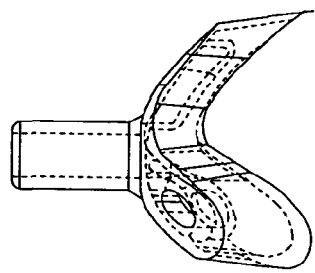
Figure 19:
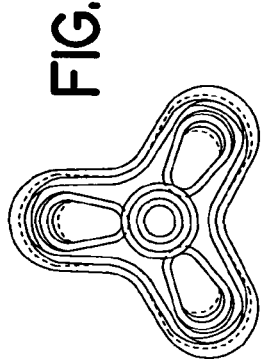
FIG. 19 is a top view of the suction pad of FIG. 18.
Figure 22:
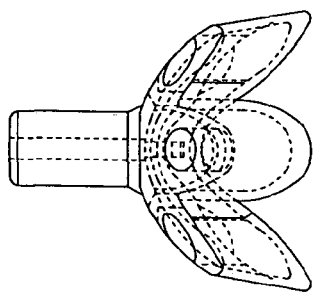
Figure 20:
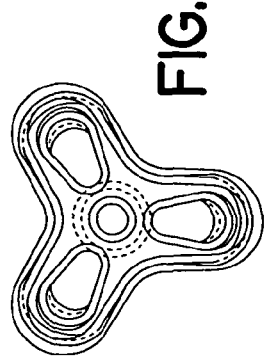
FIG. 20 is a bottom view of the suction pad of FIGS. 18 and 19.
Figure 21:
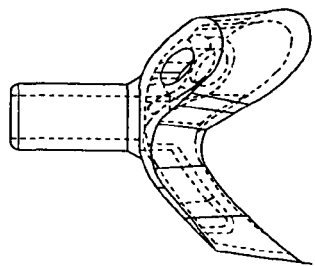
Figure 25:
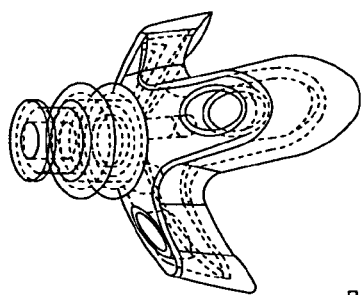
FIG. 25 is a perspective view of a third alternative embodiment of the suction pad.
Figure 31:
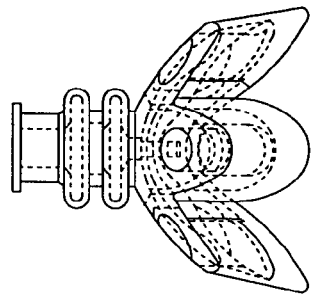
FIGS. 28-31 are front, right, back and left side views of the suction pad of FIGS. 25-27.
Figure 30:
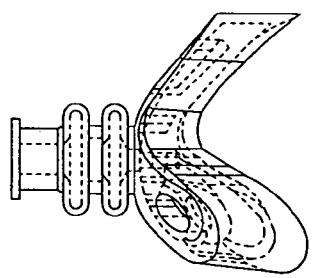
Figure 26:
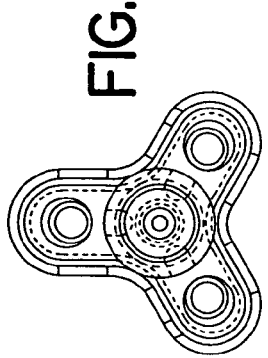
FIG. 26 is a top view of the suction pad of FIG. 25.
Figure 29:
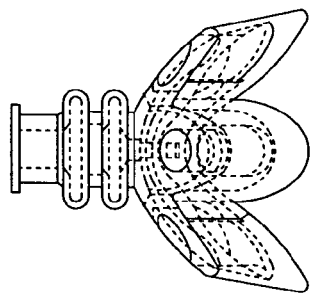
Figure 27:
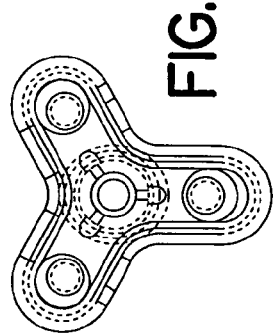
FIG. 27 is a bottom view of the suction pad of FIGS. 25 and 26.
Figure 28:
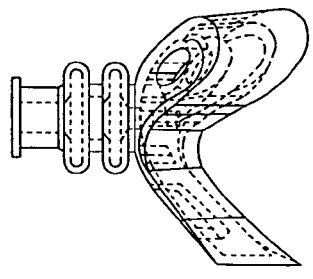
Figure 39:
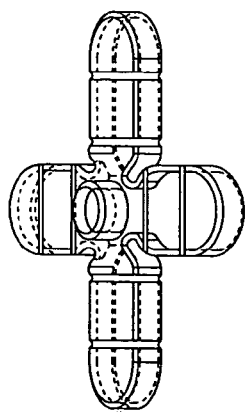
FIG. 39 is a perspective view of a fifth alternative embodiment of the suction pad.
Figure 40:
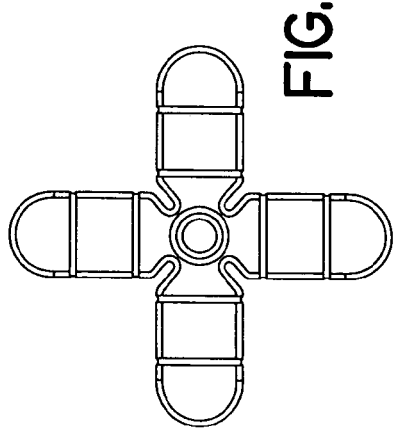
FIG. 40 is a top view of the suction pad of FIG. 39.
Figure 41:
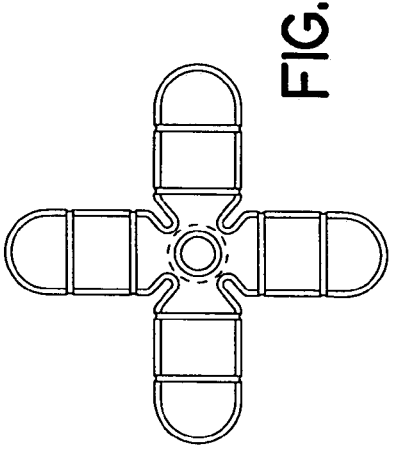
FIG. 41 is a bottom view of the suction pad of FIGS. 39 and 40.
Figure 45:
FIGS. 42-45 are front, right, back and left side views of the suction pad of FIGS. 39-41.
Figure 44:
Figure 43:
Figure 42:
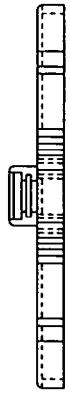

Heart positioning device 50, as shown in FIGS. 1-3, generally comprises a resiliently-flexible suction pad 52, a support arm 54 and a clamping mechanism 56 for attaching the support arm 54 to a structure, such as a retractor, that is fixed relative to a patient.

As used herein, the terms "proximal" or "proximal direction" refer to the direction along the support arm toward the clamping mechanism 56, and the terms "distal" or "distal direction" refer to the direction along the support arm 54 toward the suction pad 52.

As used herein, the terms "vacuum" or "suction" refer to negative pressure relative to atmospheric or environmental air pressure in the operating room.

The support arm 52 is preferably of the type that can readily be changed between a flexible or articulating condition and a rigid condition. The support arm 52 preferably comprises a plurality of rigid members that are free to articulate relative to one another until a central cable pulls the rigid members together to lock the support arm in a rigid condition. The cable is controlled, for example, by a handle 58 that rotates to pull tension on the cable, thereby drawing the rigid members together to lock them into position. Each rigid member has opposite ends, one of which is concave and the other of which is convex (e.g., hemispherical). The convex end of one rigid member fits into the concave end of the adjacent rigid member, and allows the member to articulate relative to the adjacent member if the central cable has not been tensioned to lock the rigid members together. Most preferably, the rigid members are not of uniform cross section, with the rigid members closer to the distal end having a smaller cross section than the rigid members closer to the proximal end. A suitable articulating mechanism could be similar to the type used in the "OCTOPUS 3"™ tissue stabilization system sold by Medtronic, Inc., Minneapolis, Minn. USA. See, also, the articulating arm mechanisms disclosed in U.S. Pat. Nos. 5,836,311; 5,927,284 and 6,015,378, co-assigned U.S. patent application Ser. No. 09/396,047, filed Sep. 15, 1999; and Ser. No. 09/678,203, filed Oct. 2, 2000, and European Patent Publication No. EP 0 993 806.

The support arm 54 is connected to the suction pad 52 to position the suction pad 52 to thereby position or hold the heart. Preferably, the mechanism 60 connecting the suction pad 52 to the support arm 54 permits the suction pad 52 to rotate on two axes relative to the support arm 54. For example, the suction pad 52 is permitted to rotate relative to the support arm 54 along a first axis A-1, and a pivotable element 60 connected to the suction pad 52 is free to pivot along a second axis A-2 generally perpendicular to the first axis A-1. The suction pad 52 is allowed to pivot along these two axes even after the support arm 54 is locked into its rigid condition.

The suction pad 52 has a plurality of legs 62 that flex to conform to the surface of the heart. The legs 62 of the suction pad 52 preferably provide a generally starfish-shaped configuration. Preferably, there are 2-4 legs and, most preferably, there are 3 legs 62. The legs 62 preferably are generally arcuate, curving downwardly away the suspension element 68 to the free ends of the legs 62. The legs 62 are sufficiently flexible that they will bend to conform to flat or curved surfaces, facilitating use of the suction pad 52 at the apex or elsewhere on the heart.

In use, the legs 62 also allow the suction pad 52 to be oriented to avoid placement over particular features of the heart anatomy, such as the cardiac arteries, or to avoid conflict with other surgical devices, such as a heart stabilizer of the type sold under the trade designation "OCTOPUS" by Medtronic, Inc., Minneapolis, Minn., USA.

Vacuum channels 64 are provided along the tissue-engaging face of the suction pad 52 in fluid communication with the legs 62 to apply suction between the legs 62 and the surface of the heart to grasp the surface. Preferably, there is at least one vacuum channel 64 in each leg 62. A vacuum passageway 66 arranged for example along the axis of rotation A-1 is in fluid communication with the vacuum channels and a tube fitting 68. A vacuum line (not shown) is connected to the tube fitting 68 bringing the vacuum passageway 66 and vacuum channels 64 into fluid communication with a conventional vacuum source (not shown).

In one aspect of the invention, the vacuum passageway 66 and vacuum channels 64 are configured to maintain suction in the other legs 62 when one leg 62 is released from the heart. Alternatively, the configuration of the passageway 66 and channels 64 can be such as to allow the suction pad 52 to be removed under vacuum suction by peeling off one leg 62 first.

In one alternative aspect of the invention, the legs are configured and sufficiently flexible that they can be drawn against one another to a collapsed position for entering into thoracic cavity through a small incision or cannula or port in closed chest surgery. In other aspects, the suction pad 52 (including legs 62) are sufficiently resiliently flexible that they will flex to allow the suction pad 52 to be pushed through a small incision or cannula, and will return to their original shape once inside the chest cavity. The invention is also applicable to open chest/split sternum surgery, in particular open chest, beating heart surgery for repositioning the heart to improve access to various coronary arteries.

Preferably, the suction pad 52 is formed of medical grade silicone or thermoplastic elastomeric material (e.g., polyurethane). The material selected most preferably has a low durometer (e.g., about 50) so that the suction pad 52 tends to conform to the surface of the heart and to flex to help seal against the heart to maintain the vacuum in the vacuum channels 64. The suction pad 52 is preferably sufficiently flexible such that the suction pad 52 draws down toward the surface of the heart more than the surface of the heart is pulled into the channels 64. Also, preferably, the suction pad is formed of substantially transparent or translucent material.

Also, preferably, the suction pad 52 is integrally molded with at least one resiliently-flexible suspension element 68 connecting the suction pad 52 to the support arm 54. The suction pad 52 and suspension element 68 may be integrally molded of the same material. As used herein, "integral" or "integrally molded" refer to constructions in which one continuous piece is formed, rather than separate pieces that are connected together (e.g., mechanically or by welding or adhesive). Most preferably, the suspension element 68 comprises a bellows type structure (also 68) that resiliently flexes to allow the suction pad 52 to move in response to beating of the heart. The suspension element 68 is expandable to allow the suction pad 52 to stretch or move toward and away from the support arm 54 in response to the beating heart. It also allows movement in other directions or rotational and twisting motions.

Most preferably, the suspension element 68 comprises a bellows that flexes as the suspension element is stretched. When the bellows flattens out, the effective spring rate of the suspension element increases, as generally illustrated in FIG. 54. Preferably, the suction passageway 66 extends through the bellows-type suspension element 68. In such preferred embodiments, the bellows provides the further advantage of keeping the suction passageway 66 open through normal stretching of the bellows. In an alternate preferred embodiment, the suspension element comprises a two-stage or multi-stage bellows providing a varying spring rate between stages, as well as a high spring rate when the bellows is stretched until flattened out.

Preferably, at least one tissue-engaging structure 70 (also referred to as a standoff) is provided within each channel 64 to prevent the channels 64 from being closed off as tissue and suction pad 52 are drawn together to allow continued fluid communication along the channels 64. In addition, a plurality of tissue engaging structures 72 are provided adjacent the orifice of the vacuum passageway 66 to prevent the orifice and tissue being drawn together to close the orifice, thereby maintaining fluid communication between the vacuum passageway 66 and the channels 64. The tissue engaging structures 72 are preferably elongate having a direction of elongation extending generally radially with respect to the orifice.

Figure 46:
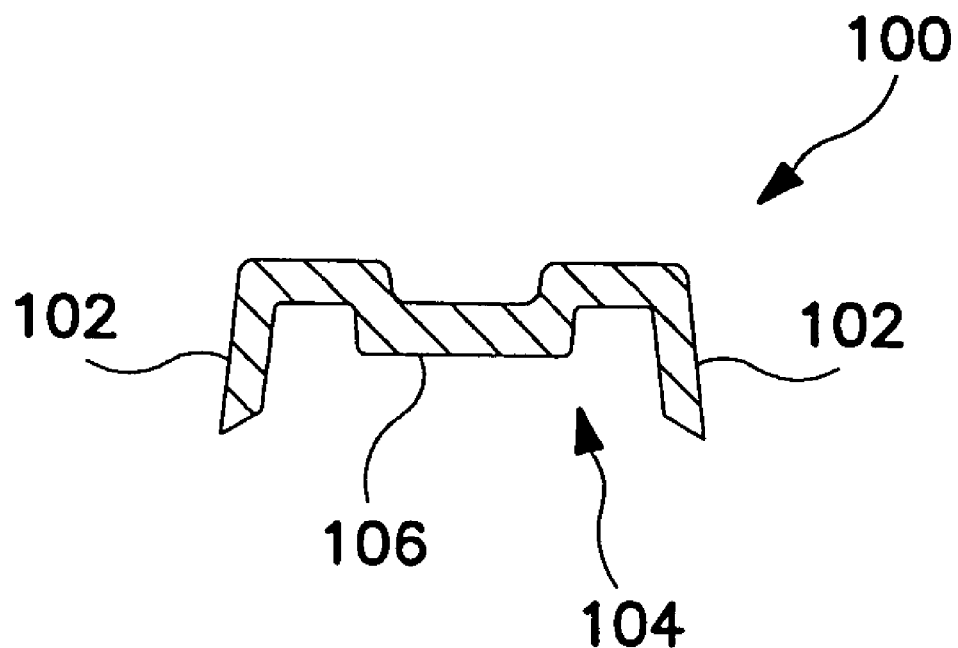
FIG. 46 shows a cross section through a preferred embodiment of the suction pad of the invention.
Figure 47:
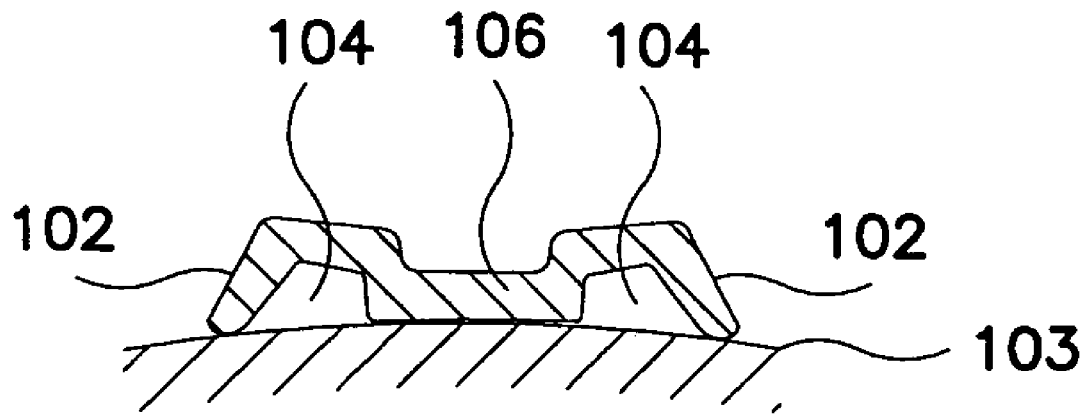
FIG. 47 is a cross section similar in some respects to FIG. 46 illustrating deformation of the suction pad against the surface of the heart.

FIGS. 46 and 47 illustrate a preferred embodiment of the suction pad, here 100, in which a resiliently flexible flange 102 resiliently deforms against heart tissue 103 to form a seal to help maintain the vacuum in the vacuum channel 104. The standoff or tissue engaging member 106 limits how far the suction pad 100 can be pulled down toward the surface of the heart to maintain the vacuum channel 104, as illustrated in FIG. 47. Most preferably, the end 108 of each flange is beveled as illustrated in FIG. 46 so that the laterally outward edge of each end 108 extends further than the laterally inward edge of each end. The flange 102 extends along substantially the entire periphery of the suction pad 100 so that vacuum can be maintained in the area defined between the flange 102, the body of the suction pad 100 and the surface of the heart.

Figure 48:
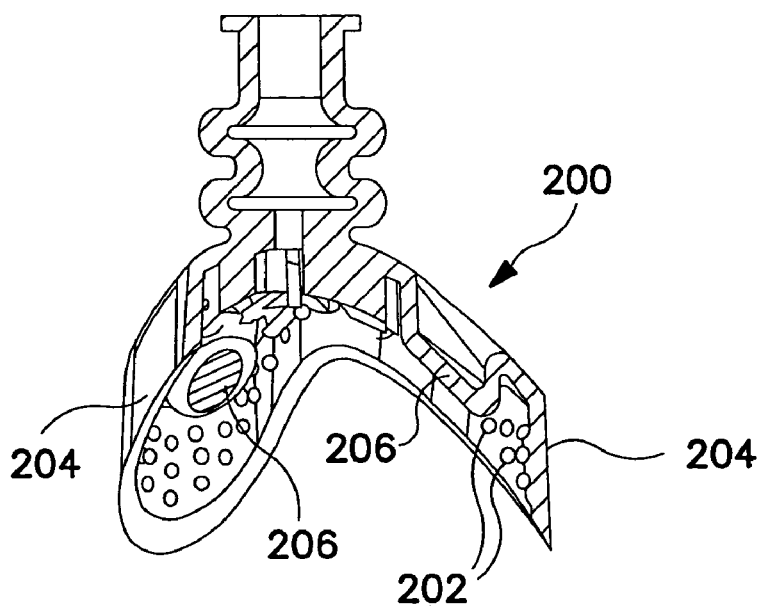
FIG. 48 is a side view of yet another suction pad of the invention with portions cut away to illustrate a dimples on the inner wall of the peripheral flange thereof.
Figure 49:
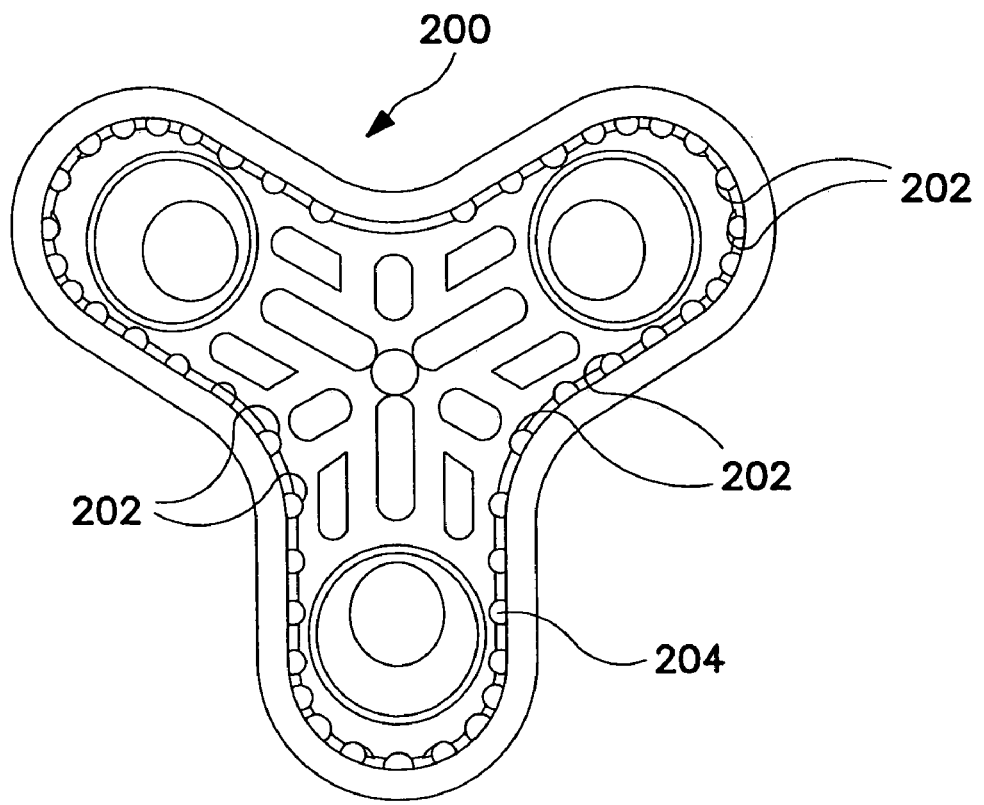
FIG. 49 is a bottom view of the suction pad of FIG. 48.

FIGS. 48 and 49 illustrate yet another embodiment of the suction pad, here designated 200, in which a plurality of bumps 202 are provided on the inner surface of a resiliently flexible peripheral flange 204. Most preferably, the bumps 202 are generally hemispherical convex structures forming an integral part of the inner surface of the peripheral flange 204. When suction is pulled through the vacuum channel, the bumps 202 are pulled against the epicardium as the flanges deforms against the epicardium. The bumps 202 help retain the suction pad 200 in place on the heart.

Most preferably, the bumps 202 may be arranged in an alternating pattern, aligned pattern or irregular pattern, for example.

Textures other than bumps are also contemplated, such as dimples, spikes, ridges, grooves (e.g., microgrooves), roughened texture (e.g., microtextured), surface grain, strips, ribs, channels, ruts, embedding or adhering abrasive particles in or on the surface, gluing or laminating the texture onto the surface, or other surface treatments, conditions or configurations that increase the grip of the inner surface of the flange 204 on the epicardium. It is also contemplated that the other underside surfaces of the suction pad, and in particular the ends of the flange, could be textured to increase surface area and/or gripping. For example, a texture is preferably provided on the tissue-engaging structures or stand-offs 206, and this texture may be in the same form as the texture on the inner surface of the peripheral flange 204 or a different gripping texture. The texture may be formed by any suitable methods, such as by molding, chemical etching, roughening with sandpaper or other abrasives (e.g., sand blasting), electrical means (such as EDM machining), thermal means, or laser etching, for example.

FIG. 50 illustrates another embodiment of the heart positioner, here designated 300, in which the tube fitting 302 includes a ninety degree bend. The tube fitting 302 receives a vacuum line. The suction pad 304 and tube fitting 302 preferably are free to rotate relative to the end 306 of the arm 308. FIG. 51 illustrates yet another embodiment of the heart positioner, here designated 400, in which a filter element 402 is provided within the tube fitting 404. The filter element 402 preferably includes a through bore 406 as illustrated in FIGS. 52 and 53.

FIGS. 55 and 56 illustrate additional embodiments of the heart positioner of the invention, in which the positioner does not include a rigid support arm. FIG. 55 illustrates a heart positioner 500 comprising a suction pad or head 502 and a vacuum tube 504, which provides vacuum to the suction head 502 and provides a tether or means for manipulating and holding the suction head 502 to position and orient the heart. FIG. 56 illustrates a heart positioner 600 comprising a suction pad or head 602, vacuum tube 604, and suture or line 606 that provides a tether or means for manipulating and holding the suction head 602 to position and orient the heart. The suture 606 is retained in a suture guide, clamp or lock 608 provided, for example, on a sternal retractor 610, although it is also contemplated that it could be retained on a rib retractor, port, cannula or other device or mechanism, or mounted on the patient, operating table or other stable or stationary object.

Figure 57:
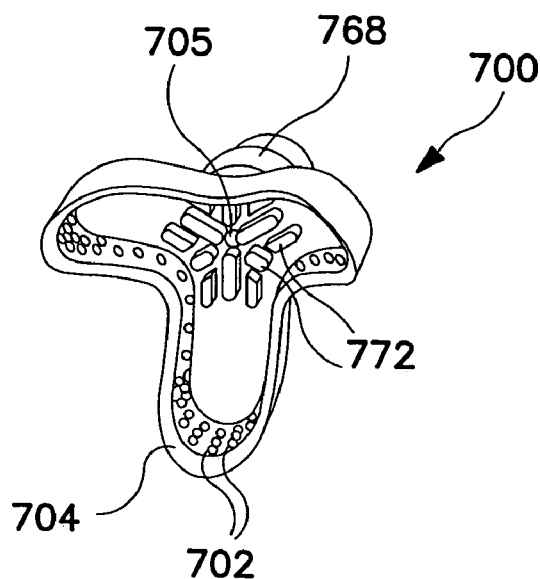
FIG. 57 is a bottom view of an alternative embodiment of the suction pad.

FIG. 57 illustrates yet another embodiment of the suction pad, here designated 700, in which a plurality of bumps 702 are provided on the inner surface of a resiliently flexible peripheral flange 704. In this embodiment, suction pad 700 includes a plurality of tissue engaging structures 772 adjacent orifice 705 of a vacuum passageway. Suction pad 700 also includes a resiliently-flexible, bellows-type suspension element 768 for connecting the suction pad to a support arm. In this embodiment, suction pad 700 and suspension element 768 are integrally molded of the same material.

Figure 58:
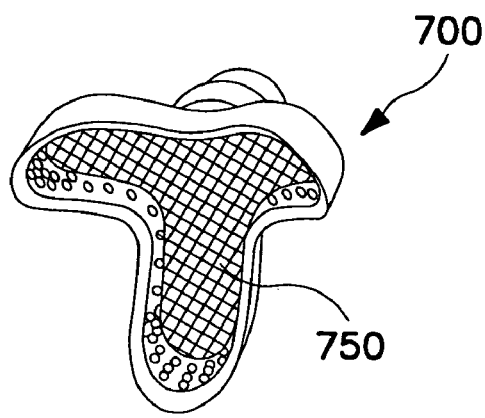
FIG. 58 is a bottom view of an alternative embodiment of the suction pad.
Figure 59:
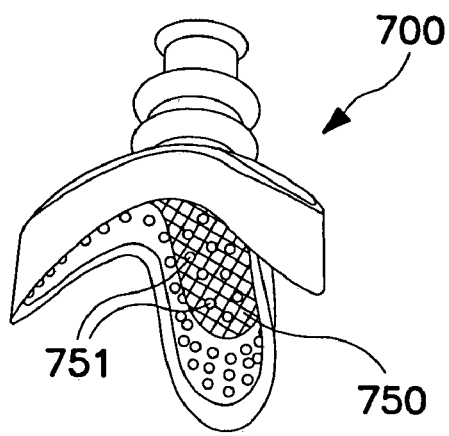
FIG. 59 is a side view of an alternative embodiment of the suction pad.

FIG. 58 illustrates yet another embodiment of the suction pad 700, in which a porous material 750 such as a porous membrane, screen, mesh, open cell foam, fabric or the like may be used to help prevent the orifice and tissue being drawn together to close the orifice, thereby maintaining fluid communication between the vacuum passageway and the vacuum channels. During operation of the device, the porous material 750 may engage tissue and may be provided with a textured surface to improve frictional contact with the tissue. The porous material 750 may be placed on top of standoffs and/or, as shown in this embodiment, may be placed on top of tissue engaging structures 772. As shown in FIG. 59, the surface of the porous material 750 may comprise bumps 751. The porous material 750 may comprise a number of materials including metallic, ceramic and/or polymeric materials. The porous material may be made of synthetic or natural materials. In one preferred embodiment of the present invention, the mesh may be made of a medical grade polyester mesh made from 70 denier thread having an opening density of about 17 openings per inch. In another preferred embodiment, open cell foams may be used with a porosity of about 10 openings per inch for thick foams (about ¼ inch thick) and about 30-50 openings per inch for thin foams (about ⅛ inch thick).

Figure 60:
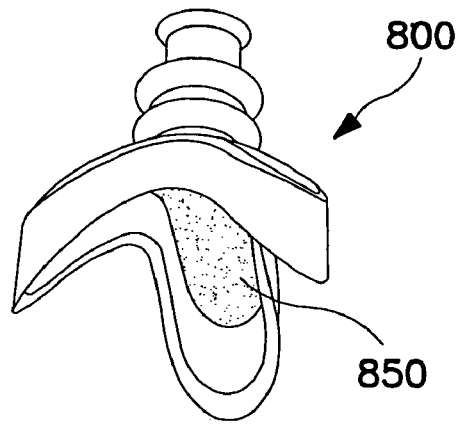
FIG. 60 is a side view of an alternative embodiment of the suction pad.

FIG. 60 illustrates yet another embodiment of the suction pad, here designated 800, in which porous foam 850 is to prevent the orifice and tissue being drawn together to close the orifice. The porous foam, e.g., a polymeric foam, may be placed on top of standoffs and/or tissue engaging structures or, as shown in this embodiment, may be placed directly over the vacuum orifice without the use of standoffs or tissue-engaging structures. Alternatively to porous foam other porous materials may be used.

Also contemplated is including a light pipe in the heart positioner to illuminate the suction pad and/or surgical field. A transparent, semi-transparent or translucent suction pad could be illuminated merely by placement of the end of a light pipe adjacent the suction pad.

Also contemplated is the provision of one device that incorporates both the dynamic heart positioning suction pad connected to a single arm along with a heart stabilizer, for example, of the type sold under the trade designation "OCTOPUS". Most preferably, however, the heart positioner and heart stabilizer are different devices, each of which may be attached for example to a common sternal retractor.

Further contemplated are embodiments in which the suction pad is molded of multiple materials of different durometers and properties, to form, for example, an endoskeleton or exoskeleton to provide varying degrees of stiffness and flexibility along different portions of the suction pad.

Also contemplated is use of a detachable or replaceable suction pad, sets of suction pads of different sizes, and/or isolated vacuum passageways to each leg.

U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000, are incorporated herein by reference.

Figure 61:
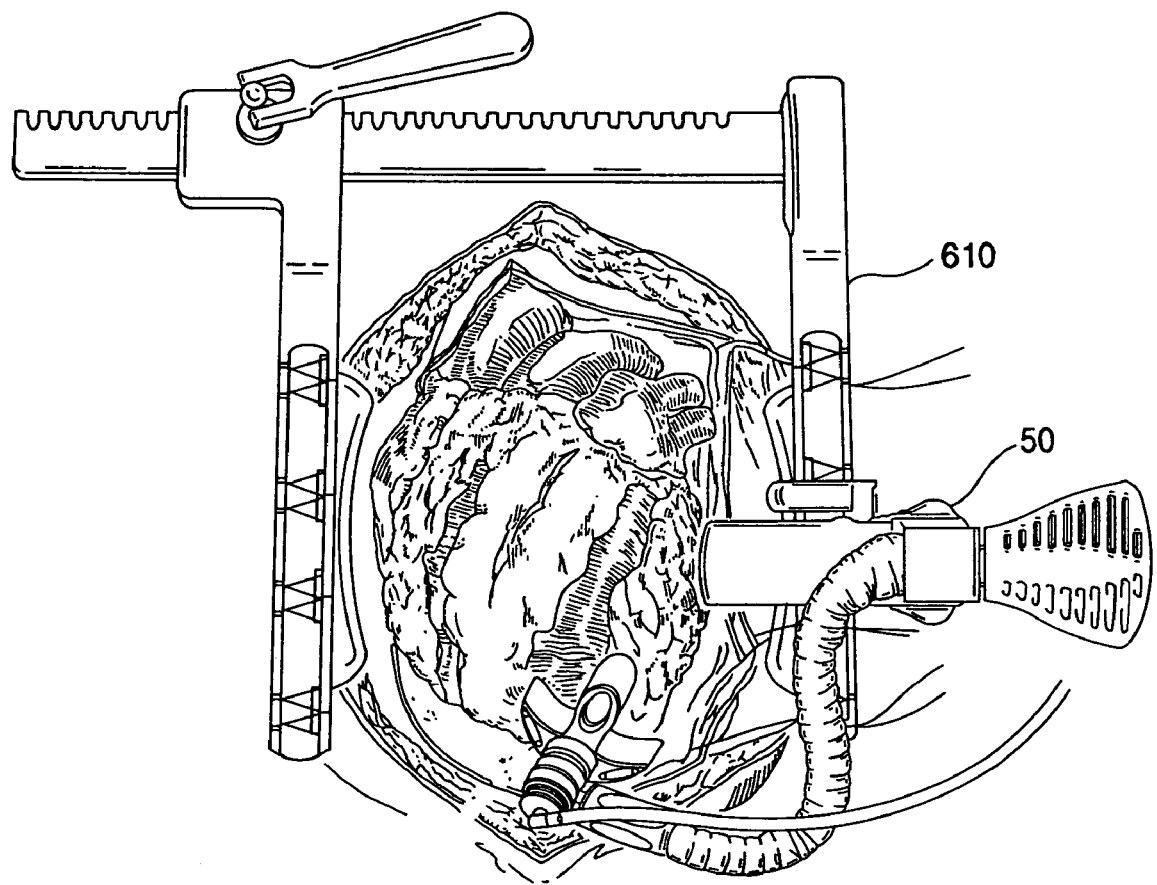
FIG. 61 is a top view of the device of the invention positioning a heart for treatment of the anterior wall of the heart.
Figure 62:
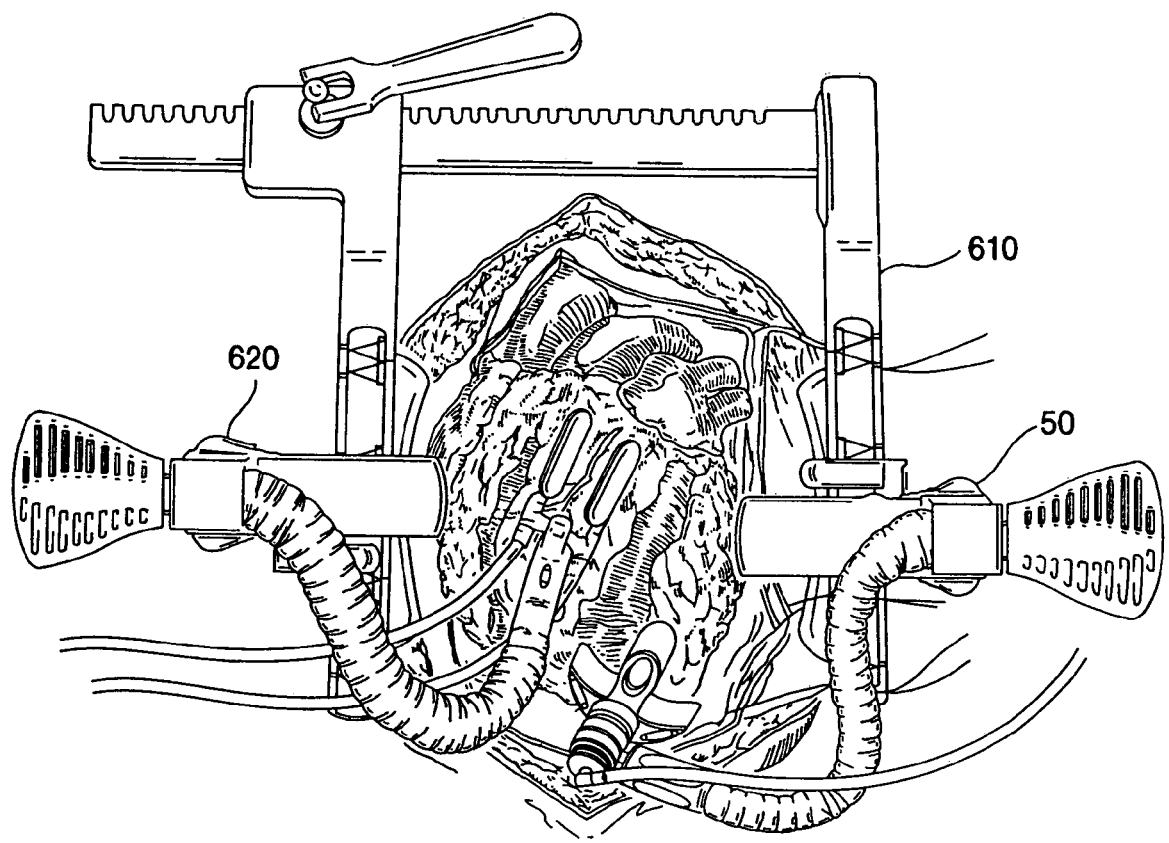
FIG. 62 is a top view of the device of FIG. 61 in cooperating relationship with an OCTOPUS® stabilization device.

In operation, the device can be used in a variety of surgical procedures to position, manipulate, stabilize and/or hold a heart. For example, in one procedure the chest is first opened by a median sternotomy or thoracotomy, which makes it possible to gain access to all chambers and surfaces of the heart. The remainder of the procedure can then be performed with the heart arrested as in traditional by-pass surgery or, more preferably, off bypass, while the heart is beating and the coronary arteries are under positive blood pressure. Repairs can be made on a beating heart by using heart stabilization systems, such as the Medtronic OCTOPUS® Tissue Stabilizer and Accessories (available from Medtronic, Inc., Minneapolis, Minn. USA), the current model being designated the "OCTOPUS 3™ stabilization system", by which suction is used to grip and immobilize the surface of the heart at or near the desired location for the surgical repair. The OCTOPUS® stabilization system also allows the surgeon to manipulate the site for surgical repair into better view by rotating and supporting the heart as set forth in e.g., U.S. Pat. Nos. 5,836,311; 5,927,284 and 6,015,378, and co-assigned U.S. patent application Ser. No. 09/396,047, filed Sep. 15, 1999, Ser. No. 09/559,785, filed Apr. 27, 2000, and Ser. No. 09/678,203, filed Oct. 2, 2000; and European Patent Publication No. EP 0 993 806, which are incorporated herein by reference in their entirety. The device of the present invention can be used in combination with a stabilization system such as the OCTOPUS® stabilization system in surgical repair procedures such as in a coronary bypass operation by positioning the heart as required by the surgeon to access the coronary arteries or other structures to be repaired. In particular, structures such as the circumflex and posterior descending arteries, which lie on surfaces of the heart that are more difficult to access in the beating heart, can be accessed by the device of the present invention. When accessing various walls of the heart, the suction pad 52 of the device can be preferably applied in one of two positions depending on the anatomy of the patient and the walls of the heart to be accessed. The first position is directly on the apex of the heart, which can be used for positioning for access to the lateral wall, posterior wall, or anterior wall of the heart. The second position is an off-apex position immediately adjacent to the apex. In particular, the device can be attached to the left ventricle immediately lateral to the apex of the heart. This particular off-apex position is especially useful for accessing the lateral wall in "apex under right hemisternum" position since even modest rightward movement of the apex greatly enhances exposure of proximal obtuse marginals. Thus, the device according to the present invention has the ability to be effectively attached to the heart not only on the apex but also to near-apex surfaces of the heart when that positioning would be desirable. Thus, the references herein to "near-apex", "near the apex of the heart" or the like includes application of the suction pad 52 onto the apex or onto other surfaces of the heart immediately adjacent to the apex. Prior to engaging the heart with the device, the device is preferably clamped by the clamping mechanism 56 onto a fixed structure such as a retractor and the support arm 54 is adjusted to the desired rigidity or flexibility. The suction pad 52 is then applied onto the heart near its apex, vacuum is applied and a portion of the heart is moved from its initial position to a second position with one hand on the device and the other hand supporting the heart until the arteries or other structures to be repaired are exposed. As the suction pad 52 is applied to the heart, a plurality of legs 62 may flex as required to conform to the surface of the heart. The legs 62 are placed on the heart by the surgeon in an orientation that avoids any interference between the legs and the arteries to be surgically repaired and also in an orientation that avoids any interference between the legs and the equipment to be used in making the surgical repair. Preferably, the suction pad 52 is placed onto the heart in a position that allows the suspension element 68 or bellows structure to be perpendicular to the weight of the portion of the heart to be positioned. Preferably, vacuum is applied after positioning the suction pad, which causes the suction pad to be drawn down toward the surface of the heart and the legs 62 to grasp the surface of the heart. The support arm 54 of the device is then used to move the portion of the heart from its initial position into the orientation desired by the surgeon. Preferably, the vacuum applied to the device should be a regulated vacuum that reaches about 400 mm Hg prior to positioning the heart. The support arm 54 is set in a rigid condition in order to hold the heart in the desired position. In this desired position, the heart continues to beat and supply blood to the patient because the device maintains the heart in a shape that does not produce marked deterioration in hemodynamic performance. Since the suction pad 52 is permitted to pivot and rotate on two axes relative to the support arm 54, the surgeon may then rotate and/or pivot the heart as required to access the area of the heart to be repaired. FIG. 61 depicts the device 50 according to the present invention clamped to a sternal retractor 610 and arranged for treatment of a heart at an anterior wall. Additional tools which stabilize and/or position the heart such as the OCTOPUS® stabilization system can also be applied adjacent to the area of the heart to be repaired in order to stabilize the heart in that area and also to further position and hold the heart in the orientation that will allow the surgeon to make the repair. FIG. 62 depicts the addition of an OCTOPUS® stabilizer 620 for stabilization of the vessel to be treated. The device may also be used by the surgeon during the procedure to reposition the heart in the event that repositioning is needed to access the sites of more than one repair or to access a repair site in a more advantageous position. Once the surgical repairs are completed, the surgeon releases any stabilization system and then releases the vacuum and removes the device while manually supporting the heart.

As various changes could be made in the above constructions and methods without departing from the scope of the invention, it is intended that all matter contained in the description or shown in the accompanying drawings be interpreted as illustrative and not in a limiting sense.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A heart positioning device comprising:
   at least three resiliently-flexible legs outwardly extending from a centrally-located suspension element, the legs capable of flexing to conform to a surface of the heart including a downwardly extending flange provided commonly along an outer margin of the legs to seal between the legs and the surface of the heart and to maintain a vacuum in a volume defined between the legs, the flange and the surface of the heart, the flange being deformable as suction is applied between the legs and the surface of the heart;
   at least one vacuum passageway in fluid communication with the legs to apply suction between the legs and the surface of the heart;
   a vacuum line connected to the vacuum passageway; and
   a support arm connected to the suspension element to thereby position or hold the heart.

2. The heart positioning device according to claim 1 wherein the flange includes an arcuately shaped edge.

3. The heart positioning device according to claim 2 wherein the arcuately shaped edge conforms the legs to a curved portion of the heart.

4. The heart positioning device according to claim 1 wherein the flange extends continuously around the margin of the legs.

5. The heart positioning device according to claim 4 wherein the continuous flange establishes a contiguous recess extending from a central location outwardly toward a free end of each leg.

6. The heart positioning device according to claim 5 wherein the contiguous recess forms at least a portion of the vacuum passageway in communication with each leg when the legs are in contact with a portion of the heart.

7. The heart positioning device according to claim 1 wherein the legs are configured and sufficiently flexible that they can be drawn against one another to a collapsed position for introduction into a small incision, cannula or port.

8. The heart positioning device according to claim 1 wherein the flange is formed of a polymeric material.

9. The heart positioning device according to claim 1 wherein the suspension element connecting the legs to the support arm is resiliently flexible.

10. The heart positioning device according to claim 9 wherein the suspension element connecting the legs to the support arm is molded from the same material as the flange.

11. The heart positioning device according to claim 9 wherein the suspension element comprises a bellows-type structure that flexes to allow the legs to move in response to beating of the heart.

12. The heart positioning device according to claim 9 wherein the suspension element flexes to allow the legs to rotate about an axis defined by the suspension element.

13. The heart positioning device according to claim 9 wherein the suspension element includes a passageway extending therethrough.

14. The heart positioning device according to claim 13 wherein the passageway is in fluid communication with the vacuum passageway.

15. The heart positioning device according to claim 1 wherein the vacuum passageway has at least one tissue-engaging structure within the vacuum passageway to prevent fluid communication with the legs from being closed off as the tissue and legs are drawn together under applied suction.

16. The heart positioning device according to claim 1 wherein the vacuum passageway is connected to the vacuum line through an orifice extending in the direction of the surface of the heart as suction is applied.

17. The heart positioning device according to claim 16 comprising a plurality of tissue engaging structures adjacent the orifice to prevent the orifice and tissue being drawn together to close the orifice.

18. The heart positioning device according to claim 1 wherein the support arm can be changed between a flexible condition and a rigid position for maintaining the end of the support arm connected to the suspension element in a stationary position.

19. The heart positioning device according to claim 1 wherein suspension element is permitted to rotate relative to the support arm along a first axis.

20. The heart positioning device according to claim 19 wherein the support arm includes a pivotable element connected to the suspension element that is free to pivot along a second axis generally perpendicular to the first axis.

21. The heart positioning device according to claim 1 also comprising a tissue-engaging porous material in fluid communication with the vacuum passageway for preventing the vacuum passageway from being closed off as the tissue and legs are drawn together.

22. The heart positioning device according to claim 21 wherein the porous material is a mesh.

23. A heart positioning device, the device being integrally molded of substantially elastomeric material and having at least three legs attached at a central portion and extending radially outwardly from the central portion, the legs having flexibility that permits them to flex to conform to a heart surface, the legs each having a flange extending along the legs to seal between each of the legs and a surface of the heart and at least one vacuum passageway adapted for fluid communication with a suction source to apply suction between the legs and the heart surface such that the flange of each leg deforms as suction is applied.

24. The heart positioning device according to claim 23 wherein the vacuum passageway is configured to maintain suction in the other legs when one leg is released from the heart surface.

25. The heart positioning device according to claim 23 wherein the legs are configured and sufficiently flexible that they can be drawn against one another to a collapsed position for introduction into a small incision, cannula or port.

26. The heart positioning device according to claim 23 wherein the flange includes an inner surface having a texture that tends to grip the surface of the heart when suction is drawn through the vacuum passageway.

27. The heart positioning device according to claim 26 wherein the texture comprises a plurality of bumps formed along an inner surface of the flange.

28. The heart positioning device according to claim 23 further comprising a centrally-located suspension element connected to the legs.

29. The heart positioning device according to claim 28 wherein the suspension element is integrally molded with the legs.

30. The heart positioning device according to claim 28 wherein the suspension element comprises a bellows-type structure that flexes to allow the legs to move in response to beating of the heart.

31. The heart positioning device according to claim 28 wherein the suspension element flexes to allow the legs to rotate about an axis defined by the suspension element.

32. The heart positioning device according to claim 28 wherein the suspension element includes a passageway extending therethrough in fluid communication with the vacuum passageway.

33. The heart positioning device according to claim 23 wherein the vacuum passageway has at least one tissue-engaging structure within the vacuum passageway to prevent fluid communication with the legs from being closed off as the tissue and legs are drawn together under applied suction.

34. The heart positioning device according to claim 23 wherein the vacuum passageway is connected to the vacuum line through an orifice extending in the direction of the heart surface as suction is applied.

35. The heart positioning device according to claim 34 comprising a plurality of tissue engaging structures adjacent the orifice to prevent the orifice and tissue being drawn together to close the orifice.

36. The heart positioning device according to claim 23 also comprising a tissue-engaging porous material in fluid communication with the vacuum passageway for preventing the vacuum passageway from being closed off as the heart surface and legs are drawn together.

37. The heart positioning device according to claim 36 wherein the porous material is formed of a metallic, ceramic or polymeric material.

38. The heart positioning device according to claim 36 wherein the porous material is a mesh.

39. The heart positioning device according to claim 36 wherein the porous material is an open cell foam.

40. The heart positioning device according to claim 36 wherein the porous material has about 10 to about 50 openings per inch.

41. The heart positioning device according to claim 36 wherein the porous material has a textured surface to promote frictional contact with the heart tissue.

* * * * *